United States Patent [19]

Katayama et al.

[11] Patent Number: 5,700,449
[45] Date of Patent: Dec. 23, 1997

[54] DENTIFRICE COMPOSITION

[75] Inventors: Yasushi Katayama; Kouji Maeda; Ryozo Nakai; Yoshiyuki Muroi; Takao Okajima, all of Tochigi-ken, Japan

[73] Assignee: Kao Corporation, Tokyo, Japan

[21] Appl. No.: 544,278

[22] Filed: Oct. 17, 1995

[30] Foreign Application Priority Data

Oct. 18, 1994 [JP] Japan .................................. 6-252031
Oct. 18, 1994 [JP] Japan .................................. 6-252032

[51] Int. Cl.$^6$ .............................. A61K 7/16; A61K 9/28; A61K 9/48
[52] U.S. Cl. ..................... 424/49; 424/50; 424/450; 424/451
[58] Field of Search ..................... 424/49–58, 451, 424/452

[56] References Cited

U.S. PATENT DOCUMENTS

| | | | |
|---|---|---|---|
| 4,344,931 | 8/1982 | Aguilar | 424/52 |
| 4,818,542 | 4/1989 | Deluca et al. | 424/491 |
| 4,917,892 | 4/1990 | Speaker et al. | 424/401 |
| 4,976,961 | 12/1990 | Norbury et al. | 424/401 |
| 5,004,595 | 4/1991 | Cherukuri et al. | 424/48 |
| 5,013,557 | 5/1991 | Tai | 424/493 |
| 5,059,416 | 10/1991 | Cherukuri et al. | 424/48 |
| 5,094,839 | 3/1992 | Lowder et al. | 424/49 |
| 5,387,415 | 2/1995 | Wunderlich et al. | 424/195.1 |
| 5,401,502 | 3/1995 | Wunderlich et al. | 424/195.1 |
| 5,543,162 | 8/1996 | Timonen et al. | 426/89 |

OTHER PUBLICATIONS

Database WPI, Derwent Publications, AN 80–66678C/38, JP-A-55 102436, Aug. 5, 1980.
Database WPI, Derwent Publications, AN 80–65038C/37, JP-A-55 100309, Jul. 31, 1980.
Database WPI, Derwent Publications, AN 91–116975/16, JP-A-4 222558, Aug. 12, 1992.
Database WPI, Derwent Publications, AN 88–D46845/07, JP-A-63 005011, Jan. 11, 1988.
Database WPI, Derwent Publications, AN 88–046845/07, JP-A-63 005011, Jan. 11, 1988.

*Primary Examiner*—Shep K. Rose
*Attorney, Agent, or Firm*—Oblon, Spivak, McClelland, Maier & Neustadt, P.C.

[57] ABSTRACT

The dentifrice composition includes capsule particles containing agar as a main component of a coat-forming substance and having an average particle size of from 0.3 to 3 mm, and vehicles for use in oral cavity. It may further contain nonionic surfactants and/or water-insoluble abrasive granules as desired.

23 Claims, 1 Drawing Sheet

FIG. 1

Line Width: 1 mm
Line Interval: 1 mm

FIG. 2

Light Source

FIG. 3

DENTIFRICE COMPOSITION

BACKGROUND OF THE INVENTION

1. Field of the Invention

The present invention relates to a dentifrice composition containing capsule particles easily broken upon toothbrushing and having a good sense of pleasant feeling and a product appearance.

2. Discussion of the Related Art

Conventionally, dentifrice compositions including various effective ingredients, such as medicinal ingredients, flavors, and pigments, have been known. In the above dentifrice compositions, gelatin, waxy substances, and agar are used for coat-forming substances of the capsule particles, and gelatin is mainly used.

Examples of the dentifrice compositions using gelatin for coat-forming substances include the following:

(1) Japanese Patent Laid-Open No. 49-453 discloses a dentifrice composition containing capsule particles filled with flavor-added materials;

(2) Japanese Patent Laid-Open No. 61-100516 discloses a toothpaste containing sealed gelatin capsule particles;

(3) Japanese Patent Laid-Open No. 61-225115 discloses double-layered capsule particles comprising a water-soluble medication as a core material, a lipophilic substance, such as a waxy substance, coating the core material, and a hydrophilic substance, such as gelatin, coating the lipophilic substance; and a composition for use in oral cavity containing the double-layered capsule particles; and (4) Japanese Patent Examined Publication No. 5-41602 discloses a halitosis preventive attaching to the mucous of the oral cavity, comprising a water-soluble film, such as gelatin, mixed with a halitosis preventing component.

Further, examples of the dentifrice compositions using waxy substances for coat-forming substances include the following:

(5) Japanese Patent Examined Publication No. 58-20928 discloses a dentifrice comprising a coating agent, such as a synthetic resin and paraffins, and a granular foaming agent or and an antifoaming agent coated therewith;

(6) Japanese Patent Examined Publication No. 50-25011 discloses a dentifrice containing a double-coat finely granular capsule particles comprising a water-soluble medication solid powder used as a core, a thermoplastic resin or a high-melting point waxy substance for forming a first coat layer on the core, and a high-melting point waxy substance, the melting point of which is lower than that of the first coat layer, for forming a second coat layer on the first coat layer;

(7) Japanese Patent Examined Publication No. 5-25011 discloses a granular dentifrice composition with variable flavoring, comprising flavor-enclosing cyclodextrin granules coated with coating substances consisting of a shellack varnish, a glycerol fatty acid ester, and a vehicle, and granular dentifrice base; and (8) Japanese Patent Laid-Open No. 1-275520 discloses a dentifrice composition containing one or more microcapsule particles comprising hydrophobic medicinal ingredients and linear saturated hydrocarbons expressed by $C_nH_{2n+2}$, the weight ratio of the hydrophobic medicinal ingredients to the linear saturated hydrocarbons being not more than 2.

Further, examples of the dentifrice compositions which may use agar as coat-forming substances include the following:

(9) Japanese Patent Laid-Open No. 55-100309 discloses a dentifrice composition containing microcapsule particles comprising silicone oils as a core substance wherein the coat layer of the capsule particles are broken upon brushing, thereby exhibiting antifoaming actions of the silicone oil;

(10) Japanese Patent Laid-Open No. 55-102436 discloses a non-transparent microcapsule particles obtainable by precipitating insoluble salts which are in at least partial embedded states in the coat layer and cover over the coat layer of the capsule particles; and (11) Japanese Patent Laid-Open No. 4-222558 (U.S. Pat. No. 5,004,595) discloses a delivery systems for conveying granules for giving a reinforced flavor and sweetener to a food composition, in which a granular flavor is used as a core, and the core is encapsulated by a matrix containing an outer hydrophilic polymer coat containing a strong sweetener.

The capsule particles to be blended in a dentifrice composition is required to have such properties that the coat of the capsule particles is broken upon use and thereby the contents thereof are released. However, in the case of producing capsule particles using gelatin as a coat-forming substance, although the coat is easily broken upon use, the capsule particles are also easily broken during production, thereby undesirably leaking the contents in the course of production. On the other hand, in the case of producing capsule particles using the waxy substances as a coat-forming substance, although the material is sufficiently durable against external force during production, the coat of the capsule particles is not easily broken by toothbrushing.

In the case where the agar is used as a coat-forming substance, problems incurred in the cases where gelatin and waxy substances are used as a coat-forming substance are eliminated. However, the microcapsule particles disclosed in Japanese Patent Laid-Open No. 55-100309 mentioned above have an average particle size of from 5 to 50 μm, and the non-transparent microcapsule particles disclosed in Japanese Patent Laid-Open No. 55-102436 have an average particle size of from 5 to 100 μm, both of which are extremely small. In the case where the particle size of the capsule particles is small, there arises a problem that the capsule particles are apt to be untrapped by the tip end of the toothbrush, so that the capsule particles remaining unbroken are liable to cause lowering of the sense of pleasant feeling.

As mentioned above, the capsule particles blended in the above dentifrice compositions not only have problems in the easiness in breaking upon use but also in their particle sizes.

SUMMARY OF THE INVENTION

Accordingly, in view of solving the above problems, an object of the present invention is to provide a dentifrice composition containing capsule particles with a suitable particle size, the capsule particles being easily broken upon use and recognizable of its presence in the oral cavity, without a sense of unfitting or a sense of foreign substances contained in the oral cavity.

In view of achieving the above object, the present inventors have found that a suitable particle size range of capsule particles using agar as a main component of a coat-forming substance for a dentifrice composition, and have completed the present invention.

The gist of the present invention is to provide a dentifrice composition containing capsule particles using agar as a main component and having an average particle size of from 0.3 to 3 mm.

BRIEF DESCRIPTION OF THE DRAWINGS

The present invention will become more fully understood from the detailed description given hereinbelow and the accompanying drawing which is given by way of illustration only, and thus, are not limitative of the present invention, and wherein.

The reference numerals in FIGS. 2 and 3 denote the following.

10 is a graduated measuring cylinder, 12 a dentifrice composition, 14 a glass tube, 21 an epoxy resin, 24 a glass tube, and "a" a thickness.

DETAILED DESCRIPTION OF THE INVENTION

The present invention will be explained detail below. In the present invention, "capsule particles" refer to those obtainable by coating the contents comprising medicinal ingredients, pigments, and flavors with a coat-forming substance.

The capsule particles contain the coat-forming substance having agar as a main component thereof. The agar preferably has a high solubility in water, and a greater preference is given to ones having solubility in water under a normal pressure and 95° C. of not less than 1, more preferably not less than 3, and particularly not less than 5, from the viewpoint of easy coat-formation procedure.

In addition, the agar preferably has a sufficient jelly strength of not less than 500 g/cm$^2$, because the resulting capsule particles are not likely to break during the production of the dentifrice composition. Incidentally, the jelly strength is evaluated by an amount of a load durable on an agar gel at a concentration of 1.5% by weight for 20 seconds per unit cm$^2$, the load being vertically applied to the agar. For example, among the agar used for food, the strip agar has a jelly strength of about 400 g/cm$^2$, and the square agar as a jelly strength of about 280 g/cm$^2$.

In the present invention, in order to improve the sense of pleasant feeling, hydrophilic polymeric substances or lipophilic polymeric substances may be added to the agar. Examples of the hydrophilic polymeric substances include gelatin, sodium alginate, carrageenan, carboxymethyl cellulose, methyl cellulose, hydroxyethyl cellulose, hydroxypropyl cellulose, hydroxypropylmethyl cellulose, gum arabic, gum guar, gum xanthane, casein, pectin, albumin, and polyvinyl alcohols. Examples of the lipophilic polymeric substances include waxy polymers, such as polyethylenes, polypropylenes, polystyrenes, polyvinyl chlorides, polyacrylic acids, polymethacrylic acids, cetyl alcohol, stearyl alcohol, ethylene glycol distearate, sorbitan tristearate, ceresin, paraffin waxes, polyolefin waxes, beeswaxes, and carnauba waxes. The hydrophilic polymeric substances and lipophilic polymeric substances may be used singly or in a combination of two or more kinds.

In the case where the hydrophilic polymeric substances or the lipophilic polymeric substances are added as the coat-forming substances in addition to the agar, the hydrophilic polymeric substances or the lipophilic polymeric substances may be added in an amount of preferably from 1 to 100 parts by weight, particularly from 1 to 20 parts by weight, based on 100 parts by weight of the agar, from the viewpoint of the stability of the contents and improvement of sense of pleasant feeling without impairing the releasing property in the oral cavity.

The contents of the capsule particles are not particularly limited as long as they are those generally used for compositions in use for oral cavity, such as dentifrices, the contents including medicinal ingredients, flavors, and pigments. In the present invention, a particular preference is given to those having lipophilic properties. The contents may take various desired forms, such as liquid, powder, or gel, depending upon the shapes of the dentifrice composition and the production methods used therefor.

The medicinal ingredients include tooth caries preventives, antibiotics, vitamins, enzymes, anti-flammatory agents. More specifically, examples thereof include sodium fluoride, tin fluoride, sodium monofluorophosphate, vitamin E, vitamin C, dextranase, mutase, sodium chloride, glycyrrhizinates, glycyrrhetinic acid, azulene, dihydrocholesterol, chlorohexidine, epichlorocholesterol, isopropylmethylphenol, trichlorocarbanilide, triclosan, halocarban, hinokitiol, allantoin, tranexamic acid, propoils, cetylpyridinium chloride, benzethonium chloride, benzalkonium chloride, sodium copper chlorophylin, and lysozyme chloride. The flavors include flavoring aldehydes, esters, and alcohols. More specifically, examples thereof include spearmint oil, peppermint oil, clove oil, sage oil, eucalyptus oil, laurel oil, cinnamon oil, lemon lime oil, grapefruit oil, menthol, carvone, methyl salicylate, ethyl salicylate, eugenol, camphor oil, ginger, ethyl acetate, diethyl ketone, eucalyptol, pepper, rose, isopropylmethylphenol, maltol, and anethole. The pigments include inorganic and organic pigments. More specifically, examples thereof include the inorganic pigments, such as cobalt blue, cobalt green, yellow iron oxide, titanium oxide, mica, zinc powder, and aluminum powder; lake pigments, such as Blue No. 1 and Red No. 2; and other pigments, such as copper chlorophyll, β-carotene, and iron complex salts of hinokitiol.

Also, the vehicles, such as fats and oils, waxes, hydrocarbons, higher fatty acids, higher alcohols, esters, essential oils, and silicone oils, may be further blended to the contents of the capsule particles.

Examples of the fats and oils include natural fats and oils, such as soybean oil, rice bran oil, jojoba oil, avocado oil, almond oil, olive oil, cacao butter, sesame oil, persic oil, castor oil, coconut oil, mink oil, beef tallow, and lard; hydrogenated oils obtained by hydrogenation of these natural fats and oils, and synthetic triglycerides, such as myristic glyceride, 2-ethylhexanoic glyceride, tricaprylic glyceride, and tricapric glyceride. Examples of the waxes include carnauba wax, whale wax, beeswax, and lanoline. Examples of the hydrocarbons include liquid paraffins, vaseline, paraffins, microcrystalline waxes, ceresin, squalane, and pristane. Examples of the higher fatty acids include lauric acid, myristic acid, palmitic acid, stearic acid, behenic acid, oleic acid, linoleic acid, linolenic acid, lanolic acid, and isostearic acid. Examples of the higher alcohols include lauryl alcohol, cetyl alcohol, stearyl alcohol, oleyl alcohol, lanoline alcohol, cholesterol, and 2-hexyldecanol. Examples of the esters include cetyl octanoate, myristyl lactate, cetyl lactate, isopropyl myristate, myristyl myristate, isopropyl palmitate, isopropyl adipate, butyl stearate, and decyl oleate. Examples of the essential oils include mentha oil, jasmine oil, camphor oil, hinoki oil, tohi oil, rue oil, turpentine oil, cinnamon oil, bergamot oil, citrus oil, calamus oil, pine oil, lavender oil, bay oil, clove oil, hiba oil, rose oil, eucalyptus oil, lemon oil, peppermint oil, and sage oil. Examples of the silicone oils include dimethylpolysiloxane.

Examples of the production methods for the capsule particles are not particularly limited, and any of conventionally known production methods, including chemical methods, such as interfacial polymerization method and in-liquid coat hardening method, physicochemical methods, such as coacervate method, and physical methods, such as fluidized bed method, may be employed. In particular, a preference is given to a double nozzle dropping method.

The capsule particles used in the present invention have an average particle size, determined by a microscope or calipers, of from 0.3 to 3 mm, more preferably from 0.5 to 3 mm, particularly from 0.5 to 2 mm. When the average particle size is less than 0.3 mm, the capsule particles are hardly broken upon brushing, so that the sense of pleasant feeling is significantly lowered and the capsule particles lose good appearance. When the average particle size exceeds 3 mm, the sense of pleasant feeling is significantly lowered and the capsule particles lose good appearance. The particle size distribution of the capsule particles is such that 80% or more desirably fall in the range of from 0.3 to 3 mm, particularly 90% or more in the above range, more particularly 95% or more in the above range.

Also, the capsule particles preferably have a breaking strength per each capsule particle of from 0.1 to 20 g, more preferably from 1 to 20 g, and particularly from 1 to 10 g. In the above range, leakage of the contents of the capsule particles during production and storage of the dentifrice composition are inhibited, and the capsule particles easily break upon use, to release contents thereof. Incidentally, the breaking strength is measured by continuously applying a load vertically onto one particle taken out from a dentifrice composition until breakage, and obtaining an amount of load at breakage of the coat layer of the capsule particles. The breaking strength of the capsule particles in the present invention is measured by using a compressive testing device "KES-F3" (manufactured by Katoh Tekkohjo), a load being applied at a velocity of 50 sec/mm.

Further, the coat ratio of the agar in the capsule particles preferably is in the range of from 1 to 30% by weight, more preferably from 1 to 15% by weight, particularly 5 to 15% by weight, within which range the capsule particles are given suitable breakability upon use, to release easily the contents thereof. Incidentally, the coat ratio is expressed by the weight percentage of the agar based on the entire weight of the capsule particles.

The amount of the capsule particles in the dentifrice composition of the present invention is preferably from 0.1 to 10% by weight, particularly from 0.5 to 5% by weight, within which range the effects of the medicinal ingredients, etc. are suitably obtained, and the sense of pleasant feeling and the appearance are good.

In addition to the above components, the dentifrice composition of the present invention may further contain other vehicles generally used for preparation for oral cavity including dentifrice, such as surfactants, abrasives, thickening agents, moisturizers, perfumes, sweeteners, preservatives, and water.

The water-insoluble abrasives are not particularly limited, as long as they are generally used as abrasives for teeth, and examples thereof include hydrogen calcium phosphate, calcium phosphate, water-insoluble sodium metaphosphate, silica, aluminum hydroxide, magnesium phosphate, calcium carbonate, calcium pyrophosphate, zeolite, complex aluminosilicates, magnesium carbonate, red oxide, and calcium sulfate, which may be used singly or in a combination of two or more kinds.

The water-insoluble abrasives preferably have a particle size of from 0.1 to 20 µm, particularly from 1 to 10 µm.

In the present invention, the above abrasives may be used without further treatment, or they may be formed into granules by binding and adhering water-insoluble abrasives to each other with or without a water-insoluble binder.

The water-insoluble abrasive granules used in the present invention refer to those obtainable by binding and adhering water-insoluble abrasives to each other with or without a water-insoluble binder.

By blending particular water-insoluble abrasive granules together with capsule particles, and selecting particular particle size ranges and compositions therefor, the water-insoluble abrasive granules act as a breaking aid for the capsule particles, so that the capsule particles can be notably easily broken upon brushing, thereby making it possible to speedily release the contents thereof into the oral cavity.

The amount of the water-insoluble abrasives in the water-insoluble abrasive granules is preferably from 10 to 90% by weight, particularly from 50 to 90% by weight, from the viewpoint of breakability of the capsule particles in the present invention.

Also, the water-insoluble binders may be any one of organic or inorganic binders. Examples of the organic binders include polysaccharides, such as hydroxycellulose, carboxymethyl cellulose, hydroxypropyl cellulose, gum xanthane, and carrageenan; water-insoluble fibers, such as natural fibers, polyvinyl chlorides, polyethylenes, polypropylenes, polystyrenes, methyl polymethacrylates, nylons, and silicones; and oils and fats, such as paraffins, higher alcohols, and waxes. In addition, examples of the inorganic binders include colloidal silica, magnesium metasilicate aluminate, bentonite, montmorillonite, kaolin, synthetic aluminum silicate, calcium silicates, aluminum hydroxide gels, alumina sols, magnesium carbonate, synthetic hydrotalcite, magnesium oxide, and magnesium hydroxide. Among them, the inorganic binders are preferred, because they are capable of stably maintaining the properties owned by the water-insoluble abrasive granules without causing significant changes. Since the granules can be simply prepared by spray granulation method, a particular preference is given to colloidal silica, magnesium metasilicate aluminate, synthetic aluminum silicate, and magnesium hydroxide.

These water-insoluble binders can be used singly or in combination of two or more kinds. In the case where the binders are used in combination, a preference is given to the combinations of a binder having a relatively granular form and acting as a vehicle, for example, magnesium metasilicate aluminate, synthetic aluminum silicate, and magnesium hydroxide, together with a binder having a strong adhesive property and acting to increase the granular strength remarkably, for example, colloidal silica and alumina sols, because in such combinations, the desired water-insoluble abrasive granules can be obtained by freely selecting the kinds and amounts of the water-insoluble abrasives while maintaining sufficient strength for achieving the purpose of the present invention.

The amount of the water-insoluble binder in the water-insoluble abrasive granules is preferably from 5 to 80% by weight, particularly from 5 to 50% by weight, in which the granules are not broken during the production of the dentifrice composition, and on the other hand give proper adhesive strength for allowing the granules to be broken by brushing.

The water-insoluble abrasive granules may further contain medicinal ingredients and pigments in the same manner as the capsule particles explained above. In cases where the above ingredients are included, the amount of the medicinal ingredients and the pigments in the water-insoluble abrasive granules is suitably from 0.01 to 10% by weight.

The production methods for the water-insoluble abrasive granules are not particularly limited, and any one of known methods, such as spray granulation methods and extrusion granulation methods, may be suitably used. Among them, a preference is given to spray granulation methods, because the obtained granular shape becomes spherical, thereby making the teeth less susceptible to damage by brushing, and the handling after production of the granules are made easy.

The water-insoluble abrasive granules have an average particle size of preferably from 50 to 500 μm, particularly from 100 to 400 μm, more particularly from 100 to 300 μm. When the average particle size is less than 50 μm, the granules are more likely to be untrapped by the tip end of the toothbrush, thereby making them difficult to be broken by a normal brushing. On the other hand, when the average particle size exceeds 500 μm, the capsules are less likely to be broken, and a sense of unfitting or a sense of foreign substances contained in the oral cavity are increased, thereby significantly lowering the sense of pleasant feeling.

Also, the water-insoluble abrasive granules preferably have a breaking strength per one granule of from 0.1 to 10 g, particularly from 1 to 10 g, within which range the breakability of the capsule particles can be increased by the breakage of the granules. The breaking strength of the abrasive granules in the present invention is measured by using a thermal stress analyzer "SS-10" (manufactured by Seiko Instruments), a given load (2 g/min) being applied until breakage.

The amount of the water-insoluble abrasive granules in the dentifrice composition of the present invention is preferably 1 to 50% by weight, particularly from 3 to 30% by weight. When the amount of the granules is less than 1% by weight, the absolute number of the granules contacting the capsule particles are decreased, so that the breaking of the capsule particles is likely to be difficult. When the amount exceeds 50% by weight, a sense of unfitting or a sense of foreign substances contained in the oral cavity (for instance, sandy feeling) are increased, thereby significantly lowering the sense of pleasant feeling.

In the dentifrice composition of the present invention, the compositional weight ratio between the capsule particles and the water-insoluble abrasive granules satisfy the following relationship:

$$\frac{\text{(Capsule particles)}}{\text{(Water-insoluble abrasive granules)}} \leq 2.$$

More particularly, the following relationship is satisfied:

$$\frac{\text{(Capsule particles)}}{\text{(Water-insoluble abrasive granules)}} \leq 1.$$

When the amount of the capsule particles exceeds the amount of the water-insoluble abrasive granules by two-folds, the absolute number of the water-insoluble abrasive granules contacting the capsule particles becomes small, thereby making it more difficult to break the capsule particles. In addition, it is more preferred that the breaking strength of the capsule particles exceeds the breaking strength of the water-insoluble abrasive granules.

Also, examples of the thickening agents include sodium salts of carboxymethyl cellulose, sodium polyacrylates, hydroxyethyl cellulose, thickened silica, montmorillonite, carrageenan, sodium alginate, gum guar, gum xanthane, and pectin.

Examples of the moisturizers include polyethylene glycol, propylene glycol, sorbitol, glycerol, maltitol, xylitol, and the like. Among them, a preference is given to glycerol and sorbitol.

Examples of the perfumes include natural perfumes such as spearmint oil, peppermint oil, wintergreen oil, sassafras oil, clove oil, sage oil, eucalyptus oil, mayonara oil, cinnamon oil, thyme oil, lemon oil, orange oil, and the like; as well as synthetic perfumes such as 1-menthol, anethole, carvone, eugenol, thymol, methyl salicylate, and the like.

Examples of the sweeteners include saccharin, sodium saccharin, stevioside, neohesperidyldihydrocarcone, berurauchine, p-methyoxycinnnamic aldehyde, glycyrrhizinates, aspartame (methyl aspartylphenylalanine), and the like.

Examples of the preservatives include benzoic acid, sodium benzoate, parahydroxybenzoic esters, and the like.

The surfactants used in the present invention are not particularly limited, and any one of those generally used in dentifrice compositions may be used. Examples thereof include ionic surfactants including acyl amino acid salts, such as sodium acyl glutamate and sodium salts of acyl N-methylglycinate, alkyl sulfates, such as sodium lauryl sulfate.

Also, in the dentifrice composition in the present invention containing capsule particles using agar as the main component of the coat-forming substances, it has been found that the use of a nonionic surfactant allows to keep the medicinal ingredients and other contents stably in the capsule particles until use, and to break the capsule particles easily during use, to release the contents, such as medicinal ingredients, in the oral cavity.

Examples of the nonionic surfactants used in the present invention include polyoxyethylene alkyl ethers, polyoxyethylene alkylaryl ethers, polyoxyethylene-polyoxypropylene alkyl ethers, polyoxyethylene-polyoxypropylene block copolymers, sucrose fatty acid esters, glycerol fatty acid esters, propylene glycol fatty acid esters, sorbitan fatty acid esters, alkylglycoside fatty acid esters, polyoxyethylene sucrose fatty acid esters, polyoxyethylene glycol fatty acid esters, polyoxyethylene sorbitan fatty acid esters, alkylglycosides, fatty acid monoethanolamide, polyoxyethylene fatty acid monoethanolamide, polyoxyethylene fatty acid diethanolamide, polyoxyethylene castor oils, polyoxyethylene hydrogenated castor oils, and polyoxyethylene beeswax derivatives. Among them, a preference is given to Polyoxyethylene-polyoxypropylene block copolymers, sucrose fatty acid esters, alkylglycosides, polyoxyethylene sucrose fatty acid esters, and polyoxyethylene hydrogenated castor oils. Further, among the above nonionic surfactants, those having low fluidity are preferred, because the amount of leakage of the contents of the capsule particles is extremely lowered. In the present invention, a greater preference is given to the polyoxyethylene-polyoxypropylene block copolymers, particularly to the Polyoxyethylene-polyoxypropylene block copolymers having an average molecular weight of from 1,000 to 15,000.

The above nonionic surfactants may be used singly or in a combination of two or more kinds. The amount of the nonionic surfactant in the dentifrice composition is preferably from 1 to 40% by weight, particularly from 3 to 30% by weight, within which range leakage of the contents of the capsule particles can be extremely lowered, to increase the stability of the capsule particles and to give a good sense of pleasant feeling, too.

The vehicles for oral cavity comprise 1 to 40% by weight of surfactants, 1 to 75% by weight of water-insoluble abrasives, not more than 5% by weight, particularly from 0.5 to 5% by weight, of thickening agents, and 10 to 85% by weight of a total amount of moisturizers and water. Further, it preferably contains perfumes and sweeteners in a total amount of from 0.01 to 5% by weight.

The dentifrice composition of the present invention may take a desired form, including toothpaste, toothpowder, and liquid dentifrice. By using a transparent agar, which is transparent with or without color depending upon pigments used, for forming the coat for the capsule particles, and making other components of the dentifrice composition transparent, a further improvement in appearance in the overall dentifrice composition is obtained by a synergistic effect of both the transparency of the capsule particles and the dentifrice composition containing the capsule particles. In the case where the dentifrice composition is made transparent as explained above, the degree of transparency, evaluated by visually observing a maximum thickness (mm) at which a double line mark can be clearly recognized, is preferably not less than 3 mm, particularly not less than 5 mm. Incidentally, the method for measuring the degree of transparency is carried out according to the method described in Examples.

Since the dentifrice composition of the present invention contains the capsule particles containing agar which is a coat-forming substance as a main component and having an average particle size of from 0.3 to 3 mm, the capsule particles are easily broken upon brushing upon use, and the contents, such as medicinal ingredients, can be released and penetrated in the oral cavity. Also, since the capsule particles are so easily broken and they have suitable particle size, the user is free from sense of unfitting or a sense of foreign substances contained in the oral cavity, thereby increasing its sense of pleasant feeling. Further, since the capsule particles have a size which can be visually confirmed, the users are provided with sense of security and anticipation for the actions of medicinal effects without having unpleasant feeling from containing foreign substances.

In addition, in the dentifrice composition of the present invention, by using a nonionic surfactant, since the leakage of the contents of the capsule particles can be extremely lowered during production and storage of the capsule particles, compositional changes are very small for a long period storage after production, thereby making it possible to maintain high quality capsule particles. Also, since the coat of the capsule particles is easily broken upon use and the contents thereof are released and the compositional changes of the contents are small, a desired amount of the contents can be administered locally in the oral cavity more surely. Moreover, the dentifrice composition of the present invention has excellent sense of pleasant feeling, thereby being particularly suitable for use in toothpastes.

The capsule particles and the water-insoluble abrasive granules are likely to be collected locally in the oral cavity upon brushing at such places as between teeth, and gaps formed between teeth and the gums. In these places, the contact frequency between the capsule particles and the water-insoluble abrasive granules is remarkably increased, thereby allowing a further smooth breaking of the capsule particles. The increase in the contact frequency is incurred by the bombardment of the granules and the capsule particles, or breaking of the granules at once, the broken granules being bombarded with the capsule particles. The breaking of the capsule particles leads to completely and extremely speedy release and penetration of the contents of the capsule particles, thereby making it possible to exhibit the effects of the medicinal ingredients more securely. Further, the water-insoluble abrasive granules also act as abrasives.

Furthermore, since the water-insoluble abrasive granules are easily broken and the capsule particles are easily breakable, each having a suitable particle size, the user has significantly lower sense of unfitting or sense of foreign substances in the oral cavity, thereby increasing its sense of pleasant feeling.

EXAMPLES

The present invention will be explained in further detail by means of the following production examples, comparative production examples, examples, and comparative examples, without intending to restrict the scope of the present invention thereto.

Production Example 1-1

Capsule particles were produced by using the following components and production method. As for agar, a product under a tradename of "UP-37" (solubility: 10; jelly strength: 700 g/cm$^2$; manufactured by Ina Shokuhin Kogyo K.K.) was used.

| Components for Capsule Particles | |
|---|---|
| Coat liquid: | |
| Agar | 5% by wt. |
| Purified Water | 95% by wt. |
| Contents liquid: | |
| Tri(caprylic acid capric acid)-glycerol*[1] | 40% by wt. |
| β-Glycyrrhetinic acid | 50% by wt. |
| Ethanol | 10% by wt. |

Note *[1] ("COCONARD MT," manufactured by Kao Corporation, which is a triglyceride of a mixture of caprylic acid and caproic acid.

Production Method for Capsule Particles

The capsule particles were produced by a double nozzle dropping method. Here, the nozzle diameter for pouring the contents liquid was set at 0.8 mm, the nozzle diameter for pouring the coat liquid was set at 1.0 mm, the temperatures for the tank containing the coat liquid and the dyne through which the coat liquid flowed were set at 75° C., and the temperature of the cooling liquid was set at 25° C.

The capsule particles obtained above had an average particle size of 1 mm, and a coat ratio of 10.2%. Here, the average particle size was determined by calipers, and the coat ratio was calculated by dividing the weight of the coat portion, obtained by breaking one capsule particle and removing contents thereof, by the entire weight of the one capsule particle. Incidentally, in the following Production Examples, unless noted otherwise, the particle size was measured by using calipers. Both of the obtained values for the average particle size and the coat ratio are averaged value for twenty capsule particles. Also, one of the capsule particles was broken to extract β-glycyrrhetinic acid contained in the contents liquid with a 0.0025M phosphoric acid-acidic methanol aqueous solution (75 v/v %), and the obtained extract was quantitatively analyzed using a high-performance liquid chromatography ("L-600," manufactured by Hitachi Ltd). As a result, the amount of β-glycyrrhetinic acid was found to be 44.9%. Here, the amount was so obtained by averaging values obtained with twenty particles as above.

Production Example 1-2

Capsule particles were produced in the same manner as in Production Example 1-1 by using the following components.

Components for Capsule Particles

| Coat liquid: | |
| --- | --- |
| Agar (The same one as in Production Example 1-1) | 10% by wt. |
| Purified Water | 90% by wt. |
| Contents liquid: | |
| Tri(caprylic acid capric acid)-glycerol | 40% by wt. |
| β-Glycyrrhetinic acid | 50% by wt. |
| Ethanol | 10% by wt. |

The capsule particles obtained above had an average particle size of 1 mm, and a coat ratio of 36.2%. The amount of β-glycyrrhetinic acid in one capsule particle was quantitatively analyzed in the same manner as in Production Example 1-1, and it was found to be 31.9%.

Production Example 1-3

Capsule particles were produced using the same components as in Production Example 1-1 and a production method given below.

The capsule particles were produced by a double nozzle dropping method similar to that in Production Example 1-1, except for the following changes: The nozzle diameter for pouring the contents liquid was set at 0.25 mm, and the nozzle diameter for pouring the coat liquid was set at 0.35 mm.

The capsule particles obtained above had an average particle size of 0.35 mm, the particle size being determined by a microscope, and a coat ratio of 10.8%. The amount of β-glycyrrhetinic acid in one capsule particle was quantitatively analyzed in the same manner as in Production Example 1-1, and it was found to be 44.6%.

Comparative Production Example 1-1

Of the capsule particles produced by the method of Production Example 1-3, the particles having a particle size of less than 0.3 mm was collected by classifying with a mesh-sieve. The capsule particles obtained above had an average particle size of 0.24 mm, the particle size being determined by a microscope, and a coat ratio, which was the same as in Production Example 1-3, of 10.8%. The amount of β-glycyrrhetinic acid in one capsule particle was quantitatively analyzed in the same manner as in Production Example 1-1, and it was found to be 43.6%.

Comparative Production Example 1-2

Capsule particles were produced using the same components as in Production Example 1-1 and a production given below.

The capsule particles were produced by a double nozzle dropping method similar to that in Production Example 1-1, except for the following changes: The nozzle diameter for pouring the contents liquid was set at 2.80 mm, and the nozzle diameter for pouring the coat liquid was set at 3.50 mm.

The capsule particles obtained above had an average particle size of 3.50 mm, and a coat ratio of 9.8%. The amount of β-glycyrrhetinic acid in one capsule particle was quantitatively analyzed in the same manner as in Production Example 1-1, and it was found to be 45.1%.

Examples 1-1 to 1-4 and Comparative Examples 1-1 and 1-2

Each of the dentifrice compositions comprising a composition (expressed by "percent (%) by weight") given in Table 1-1 was prepared by a conventional method. Each of the dentifrice composition was subject to various tests evaluated by the methods explained below. Incidentally, the reason why the found values of the particle sizes differed from those given in Production Examples and Comparative Examples was owing to the fact that the agar absorbed water, thereby increasing its apparent particle size. The results are shown in Table 1-1.

(1) Measurements for Particle Size, Coat Ratio, and Breaking Strength

The found values for the measurements for particle size, coat ratio, and breaking strength were obtained for twenty capsule particles, each of the measurement method being explained in detail above, and an average value thereof was obtained.

(2) Degree of Transparency

Figure 1:
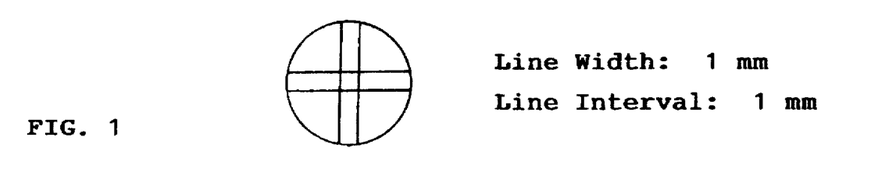
FIG. 1 is a schematic view explaining a method for measuring a degree of transparency.
Figure 2:
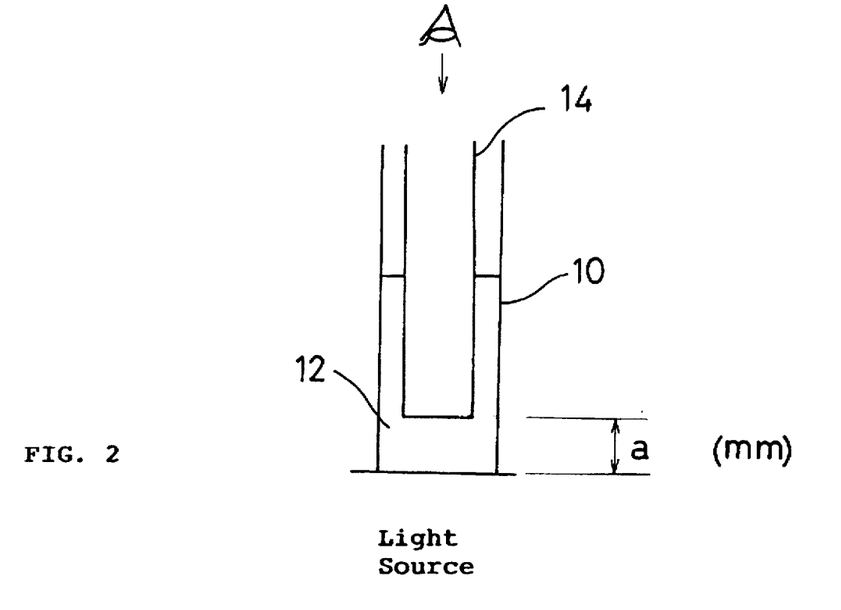
FIG. 2 is a schematic view explaining a method for measuring a degree of transparency.

The testing method for the degree of transparency is given below by referring to FIGS. 1 and 2. First, a dentifrice composition was placed in a graduated measuring cylinder 10 marked in the bottom portion as shown in FIG. 1. Next, while immersing a glass tube having a bottom portion plugged with a flat, colorless, transparent glass plate in the inner portion of the graduated measuring cylinder 10, a visual observation was made from the upper opening of the glass tube to determine a degree of transparency expressed in a thickness "a" (mm), the final point at which the double lines were clearly recognized (See FIG. 2). Incidentally, during testing, a light source was provided from two 40 Watt fluorescent lights via a frosted glass.

(3) Amount of Release of β-Glycyrrhetinic Acid (Breakability)

Figure 3:
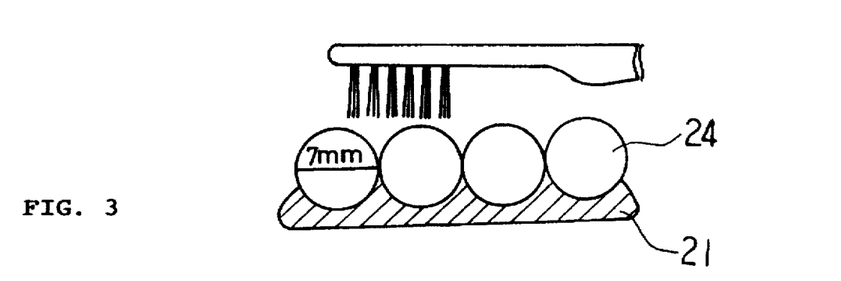
FIG. 3 is a schematic view explaining a testing method for measuring an amount of release of the contents of the capsule particles.

First, as shown in FIG. 3, a number of glass tubes (teeth), each having a diameter of 7 mm and a length of 80 mm, were pasted and fixed on an epoxy resin basement (gum), to prepare a teeth model. Next, 1 g of each of the dentifrice compositions above was accurately weighed on a toothbrush, and toothbrushing was carried out by scrubbing for three or four strokes in one second with a given load (300 grams per brushed portion). After carrying out the brushing treatment for one minute or three minutes, the amount of release of β-glycyrrhetinic acid was evaluated by a method similar to that of Production Example 1-1. The amount of release (percent by weight) was expressed as the proportion of the found value based on the weight of β-glycyrrhetinic acid.

(4) Sensory Tests

Each of the dentifrice compositions of Examples and Comparative Examples was tested by 15 persons each of male and female users, a total of 30 individuals, anywhere in the ages of from 20- to 40-years old. The sense of feeling (or sense of unfitting or sense of foreign substances contained in the oral cavity) and dentifrice composition appearance were subjected to sensory tests by the following standards. The evaluation was made by collecting each of the individual scores and averaging for each dentifrice composition.

[Sense of Pleasant Feeling (sense of unfitting or sense of foreign substances)]
1: None.
2: Almost none.
3: Slight.
4: Some feeling.
5: Strong feeling.

[Appearance of Dentifrice Composition]
1: Good.
2: Fair.
3: Hard to say good or poor.
4: Somewhat poor.
5: Poor.

TABLE 1-1

|  | Examples | | | | Comparative Examples | |
|---|---|---|---|---|---|---|
|  | 1-1 | 1-2 | 1-3 | 1-4 | 1-1 | 1-2 |
| Capsule Particles | | | | | | |
| Production Example 1-1 | 2.0 | — | 2.0 | — | — | — |
| Production Example 1-2 | — | 2.0 | — | — | — | — |
| Production Example 1-3 | — | — | — | 2.0 | — | — |
| Comparative Production Example 1-1 | — | — | — | — | 2.0 | — |
| Comparative Production Example 1-2 | — | — | — | — | — | 2.0 |
| Calcium carbonate | 30.0 | 30.0 | — | 30.0 | 30.0 | 30.0 |
| Abrasive Silica | — | — | 25.0 | — | — | — |
| Sorbitol Solution | 20.0 | 20.0 | 45.0 | 20.0 | 20.0 | 20.0 |
| Glycerol | 10.0 | 10.0 | 20.0 | 10.0 | 10.0 | 10.0 |
| Sodium Salt of Carboxymethyl Cellulose | 0.8 | 0.8 | 0.8 | 0.8 | 0.8 | 0.8 |
| Sodium lauryl sulfate | 1.2 | 1.2 | 1.2 | 1.2 | 1.2 | 1.2 |
| Sodium saccharin | 1.0 | 1.0 | 1.0 | 1.0 | 1.0 | 1.0 |
| Methyl p-hydroxybenzoate | 0.2 | 0.2 | 0.2 | 0.2 | 0.2 | 0.2 |
| Perfume | 0.8 | 0.8 | 0.8 | 0.8 | 0.8 | 0.8 |
| Purified Water | Bal. | Bal. | Bal. | Bal. | Bal. | Bal. |
| (Total) | 100.0 | 100.0 | 100.0 | 100.0 | 100.0 | 100.0 |
| Properties for Capsule Particles | | | | | | |
| Particle Size (mm) | 1.10 | 1.13 | 1.07 | 0.37 | 0.24 | 3.72 |
| Coat Ratio (% by weight) | 10.2 | 36.2 | 10.2 | 10.8 | 10.8 | 9.8 |
| Breaking Strength (g/particle) | 7.8 | 17.6 | 8.2 | 15.6 | 21.7 | 1.8 |
| Degree of Transparency (mm) | — | — | 6.5 | — | — | — |
| Amount of Release (% by wt.) | | | | | | |
| After Brushing for 1 min. | 70.3 | 59.6 | 68.7 | 61.4 | 27.9 | 88.1 |
| After Brushing for 3 min. | 93.2 | 82.3 | 91.9 | 85.6 | 54.2 | 97.6 |
| Sensory Tests | | | | | | |
| Sense of Pleasant Feeling | 1.2 | 2.1 | 1.3 | 1.5 | 3.8 | 4.3 |
| Appearance | 2.3 | 2.5 | 1.4 | 2.1 | 3.1 | 3.6 |

As is clear from Table 1-1, in the case where the particle size of the capsule particles was smaller than 0.3 mm (Comparative Example 1-1), since the capsule particles are difficult to be broken upon brushing, the amount of release of the contents was small. Further, the capsule particles remaining in the oral cavity unbroken led to the undesirable increase in the sense of unfitting or the sense of foreign substances therein.

In addition, in the case where the particle size of the capsule particles was larger than 3 mm (Comparative Example 1-2), since the capsule particles are easily breakable upon brushing, the amount of release was large. However, since individuals who carried out the tests had the sense of unfitting or the sense of foreign substances in the oral cavity due to presence of the capsule particles yet to be broken during use, and also due to a large amount of agar remaining after breaking of the capsule particles, the sense of feeling was lowered and the product appearance was poor. From the above results, it was confirmed that all of the products containing capsule particles having an average particle size outside the range of from 0.3 to 3 mm had poor quality.

Incidentally, in the case where the coat ratio exceeds 30% by weight (Example 1-2), the capsule particles were slightly less likely to be broken, thereby showing an amount of release of contents thereof relatively smaller than those of Examples 1-1 and 1-3. Also, in the case where the degree of transparency was not less than 3 mm, the individuals who carried out the test had particularly excellent sense of feeling.

Production Example 2-1

Capsule particles were produced by using the following components and production method. As for agar, the same one used for Production Example 1-1 was used.

| Components for Capsule Particles | |
|---|---|
| Coat liquid: | |
| Agar | 5% by wt. |
| Purified Water | 95% by wt. |
| Contents liquid: | |
| Tri(caprylic acid capric acid)-glycerol*[1] | 40% by wt. |
| 1-Menthol | 50% by wt. |
| Ethanol | 10% by wt. |

Note *[1]("COCONARD MT," manufactured by Kao Corporation, which is a triglyceride of a mixture of caprylic acid and caproic acid.

Production Method for Capsule Particles

The capsule particles were produced by a double nozzle dropping method. Here, the nozzle diameter for pouring the contents liquid was set at 0.8 mm, the nozzle diameter for pouring the coat liquid was set at 1.0 mm, the temperatures for the tank containing the coat liquid and the dyne through which the coat liquid flowed were set at 75° C., and the temperature of the cooling liquid was set at 25° C.

The capsule particles obtained above had an average particle size of 1 mm, and a coat ratio of 8.5%. Here, the average particle size and the coat ratio was evaluated in the same manner as in Production Example 1-1. Also, one of the capsule particles was broken, and the contents were quantitatively analyzed for the amount of 1-menthol contained therein using a high-performance liquid chromatography ("5890," manufactured by Yokokawa-Hewlett-Packard, Ltd.). As a result, the amount of 1-menthol was found to be 45.8%. Here, the amount was so obtained by averaging values obtained with twenty particles as above. In the capsule particles obtained above, since the agar had excellent coat-formability and jelly strength, the loss of the contents during production was small.

Production Example 2-2

Capsule particles were produced in the same manner as in Production Example 2-1 by using the following components.

Components for Capsule Particles

| Coat liquid: | |
|---|---|
| Agar (The same one as in Production Example 1-1) | 5% by wt. |
| Purified Water | 95% by wt. |
| Contents liquid: | |
| Tri(caprylic acid capric acid)-glycerol | 40% by wt. |
| Sodium copper chlorophylin | 50% by wt. |
| Ethanol | 10% by wt. |

The capsule particles obtained above had an average particle size of 1 mm, and a coat ratio of 9.8%. Also, one of the capsule particles was broken, and the contents were quantitatively analyzed for the amount of sodium copper chlorophylin contained therein using a high-performance liquid chromatography ("L-600," manufactured by Hitachi Ltd). As a result, the amount was found to be 45.1%. Here, the amount was so obtained by averaging twenty particles as above.

cl Comparative Production Example 2-1

Capsule particles were produced in the same manner as in Production Example 2-1 by using the following components.

| Components for Capsule Particles | |
|---|---|
| Coat liquid: | |
| Gelatin | 30% by wt. |
| Purified Water | 70% by wt. |
| Contents liquid: | |
| Tri(caprylic acid capric acid)-glycerol | 40% by wt. |
| l-Menthol | 50% by wt. |
| Ethanol | 10% by wt. |

The capsule particles obtained above had an average particle size of 1 mm, and a coat ratio of 21.5%. The amount of l-menthol in one capsule particle was quantitatively analyzed in the same manner as in Production Example 2-1, and the amount of l-menthol was found to be 39.3%. The gelatin used in this comparative example had poor jelly strength, so that the loss of the contents during production of the capsule particles was large.

Comparative Production Example 2-2

Capsule particles, each consisting of 80% by weight of hydrogenated castor oil and 20% by weight of sodium copper chlorophylin, were produced by the following method.

First, the given amount of sodium copper chlorophylin was well dispersed in melted hydrogenated castor oil. Thereafter, the obtained mixture was sprayed and cooled, to give capsule particles having an average particle size of 1 mm. The amount of sodium copper chlorophylin in one capsule particle was quantitatively analyzed in the same manner as in Production Example 2-2, and the amount of sodium copper chlorophylin was found to be 20.1%.

Examples 2-1 to 2-4 and Comparative Examples 2-1 to 2-4

Each of the dentifrice compositions comprising components shown in Table 2-1 (expressed in % by weight) was produced by a conventional method, to carry out the following test examples.

Test Example 2-1

Each of the dentifrice compositions of Examples and Comparative Examples was stored at 40° C., and the amount of the contents of the capsule particles (l-menthol or sodium copper chlorophylin) leaking in the dentifrice base material (the amount being expressed by percent by weight) was measured with respect to time by methods similar to those in Production Examples 2-1 and 2-2, to thereby evaluate stability of the capsule particles. The results are given in Table 2-1 together with the result of measurements of the breaking strength according to the method explained above. Here, the values were obtained by averaging those obtained for twenty particles.

TABLE 2-1

| | Examples | | | | Comparative Examples | | | |
|---|---|---|---|---|---|---|---|---|
| | 2-1 | 2-2 | 2-3 | 2-4 | 2-1 | 2-2 | 2-3 | 2-4 |
| Capsule Particles | | | | | | | | |
| Production Example 2-1 | 2.0 | — | — | — | — | — | — | — |
| Production Example 2-2 | — | 2.0 | 2.0 | 2.0 | — | — | — | — |
| Comparative Production Example 2-1 | — | — | — | — | 2.0 | — | 2.0 | — |
| Comparative Production Example 2-2 | — | — | — | — | — | 2.0 | — | 2.0 |
| Abrasive Silica | 20.0 | 20.0 | 20.0 | 20.0 | 20.0 | 20.0 | 20.0 | 20.0 |
| Sorbitol Solution | 25.0 | 25.0 | 25.0 | 25.0 | 25.0 | 25.0 | 25.0 | 25.0 |
| Glycerol | 10.0 | 10.0 | 10.0 | 10.0 | 10.0 | 10.0 | 10.0 | 10.0 |
| Nonionic Surfatant(*) | 20.0 | 20.0 | 1.2 | — | 20.0 | 20.0 | — | — |
| Nonionic Surfatant(**) | — | — | — | 1.2 | — | — | — | — |
| Sodium Salt of Carboxymethyl Cellulose | — | — | 0.8 | 0.8 | — | — | 0.8 | 0.8 |
| Sodium lauryl sulfate | — | — | — | — | — | — | 1.2 | 1.2 |
| Sodium saccharin | 1.0 | 1.0 | 1.0 | 1.0 | 1.0 | 1.0 | 1.0 | 1.0 |
| Methyl p-hydroxy-benzoate | 0.2 | 0.2 | 0.2 | 0.2 | 0.2 | 0.2 | 0.2 | 0.2 |
| Perfume | 0.8 | 0.8 | 0.8 | 0.8 | 0.8 | 0.8 | 0.8 | 0.8 |
| Purified Water | Bal. | Bal. | Bal. | Bal. | Bal. | Bal. | Bal. | Bal. |
| (Total) | 100.0 | 100.0 | 100.0 | 100.0 | 100.0 | 100.0 | 100.0 | 100.0 |
| Breaking Strength of Capsule Particles (g/particle) | 8.2 | 7.9 | 7.9 | 7.9 | 5.3 | 30.1 | 5.3 | 30.1 |
| Amount of Leakage (% by weight) | | | | | | | | |
| After One Month | 2.6 | 2.4 | 1.8 | 2.2 | 21.5 | 0.9 | 48.7 | 20.8 |
| After Three Months | 5.4 | 4.1 | 2.0 | 4.7 | 48.9 | 9.8 | 79.6 | 51.7 |
| After Six Months | 9.6 | 6.8 | 2.4 | 9.3 | 71.4 | 27.2 | 92.1 | 80.9 |

Note
(*): Polyoxyethylene-polyoxypropylene block copolymer (average molecular weight 10000)
(**): Laurylglucoside (degree of polymerization of glucoside: 1.4)

As is clear from Table 2-1, the leakage of the contents was extremely small, and only in the case where the capsule particles had both agar as the coat-forming substance and the nonionic surfactants.

Test Example 2-2

The dentifrice compositions of Example 2-2 and Comparative Example 2-2 were used to measure the amount of release of the contents (sodium copper chlorophylin) during use by the following method, to evaluate easiness of contents release.

First, as shown in FIG. 3, a number of glass tubes (teeth) having 7 mm diameter and 80 mm length were pasted and fixed to an epoxy resin basement (gum), to prepare a teeth model. Next, 1 g of each of the dentifrice compositions above was accurately weighed on a toothbrush, and toothbrushing was carried out by scrubbing for three or four strokes in one second with a given load (300 grams per brushed portion). After carrying out the brushing treatment for one minute or three minutes, the amount of release of sodium copper chlorophylin was evaluated by a method similar to that of Production Example 2-2. The amount of release (percent by weight) was expressed as the proportion of the found value to the weight of sodium copper chlorophylin blended upon capsule particle formation. The results are given in Table 2-2.

TABLE 2-2

|  | Amount of Release (% by wt.) | |
| --- | --- | --- |
|  | After Brushing for 1 min. | After Brushing for 3 min. |
| Example 2-2 | 68.4 | 92.8 |
| Comparative Example 2-2 | 8.2 | 18.7 |

As is clear from Table 2-2, when the dentifrice compositions of Example 2-2 and Comparative Examples 2-2 were compared, the one containing agar as the coat-forming substance (Example 2-2) had a notably larger amount of release. Also, although the differences in the amounts of release between Example 2-2 and Comparative Example 2-4 were small, the dentifrice compositions greatly differed in the stability, and the former had better sense of pleasant feeling than the latter upon actual use of the dentifrice compositions.

Production Example 3-1

(Toothpaste composition)

A toothpaste composition comprising the following composition (expressed by % by weight) was prepared by a conventional method.

| Capsule particles[1] | 2.0% by wt. |
| --- | --- |
| Water-Insoluble Abrasive Granules[2] | 6.0% by wt. |
| Glycerol | 30.0% by wt. |
| Polyoxyethylene-Polyoxypropylene Block Copolymer (Avg. MW: 10,000) | 20.0% by wt. |
| Sodium lauryl sulfate | 0.1% by wt. |
| Carrageenan | 0.2% by wt. |
| Sodium saccharin | 1.0% by wt. |
| Methyl p-hydroxybenzoate | 0.2% by wt. |
| Flavor | 0.8% by wt. |
| Purified Water | Balance |

(1) The capsule particles were prepared by the following method.

| Components for Capsule Particles | |
| --- | --- |
| Coat liquid: | |
| Agar (Solubility: 1.2; jelly strength: 900 g/cm²) | 5% by wt. |
| Purified Water | 95% by wt. |
| Contents liquid: | |
| Tri(caprylic acid capric acid)-glycerol) (One used in Production Example 1-1) | 90% by wt. |
| Vitamin E | 10% by wt. |

Production Method for Capsule Particles

The capsule particles were produced by a method similar to that of Production Example 1-1 except for making the following changes. Here, the nozzle diameter for pouring the contents liquid was set at 0.40 mm, the nozzle diameter for pouring the coat liquid was set at 0.50 mm. The capsule particles obtained above had an average particle size of 0.50 mm, the particle size being determined by a microscope, a coat ratio of 8.5%, and a breaking strength per one particle of 5.5 g.

(2) The water-insoluble abrasive granules were prepared by the following method.

A water slurry containing 60% by weight of abrasive silica used as a water-insoluble abrasive, 30% by weight of synthetic aluminum silicate used as a water-insoluble binder, and 10% by weight of colloidal silica, the water slurry having a water content of about 60% by weight, was placed in an agitation mixer. After agitating and blending the components for 120 minutes, water-insoluble abrasive granules were produced by using a spray granulator. Ninety-nine percent of the entire granules had a particle size falling in the range of from 50 to 500 μm, the average particle size being 220 μm.

The breaking strength per one particle of the abrasive granules was measured by using a thermal stress analyzer "SS-10" (manufactured by Seiko Instruments), a given load (2 g/min) being applied until breakage. As a result, the breaking strength per one particle was found to be 6.2 g.

The degree of transparency of the obtained toothpaste composition was evaluated in the same manner as in Example 1-1, and it was found to be 5.5 mm.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A capsule, comprising:
   (i) a coating comprising agar; and
   (ii) a dentifrice ingredient, encapsulated by said coating, wherein said capsule has an average size of from 0.3 to 3 mm.

2. The capsule of claim 1, wherein said dentifrice ingredient is a medicinal ingredient, a flavoring agent or a pigment.

3. The capsule of claim 2, wherein said medicinal ingredient is a tooth caries preventative, an antibiotic, a vitamin, an enzyme or an anti-inflammatory agent.

4. The capsule of claim 1, wherein said coating comprises agar as the main component.

5. The capsule of claim 1, wherein said capsule has an average particle size of 0.5 to 3 mm.

6. The capsule of claim 1, wherein said agar has a jelly strength of not less than 500 g/cm$^{-2}$.

7. The capsule of claim 1, wherein said agar comprises 1 to 30% by weight of said capsule.

8. The capsule of claim 1, wherein said capsule has a breaking strength of 1 to 20 g.

9. The capsule of claim 1, wherein said coating further comprises a hydrophilic or lipophilic polymer.

10. The capsule of claim 9, wherein said hydrophilic or lipophilic polymer is selected from the group consisting of gelatin, sodium alginate, carrageenan, carboxymethyl cellulose, methyl cellulose, hydroxyethyl cellulose, hydroxypropyl cellulose, hydroxypropylmethyl cellulose, gum arabic, gum guar, gum xanthane, casein, pectin, albumin, polyvinyl alcohols, polyethylenes, polypropylenes, polystyrenes, polyvinyl chlorides, polyacrylic acids, polymethacrylic acids, cetyl alcohol, stearyl alcohol, ethylene glycol distearate, sorbitan tristearate, ceresin, paraffin waxes, polyolefin waxes, beeswaxes and carnauba wax.

11. The capsule of claim 9, wherein said coating comprises 100 parts by weight of said agar and 1 to 20 parts of said hydrophilic or lipophilic polymer.

12. A dentifrice composition, comprising:
   (a) 0.1 to 10% by weight of capsules, comprising:
      (i) a coating comprising agar, and
      (ii) a dentifrice ingredient, encapsulated by said coating,
   wherein said capsules have an average size of from 0.3 to 3 mm and are easily broken upon brushing teeth; and
   (b) a dentifrice vehicle, comprising:
      (i) 1 to 40% by weight of at least one surfactant, and
      (ii) 1 to 75% by weight of water-insoluble abrasives,
   wherein said abrasives break said capsules upon brushing teeth.

13. The composition of claim 12, wherein said dentifrice ingredient is a medicinal ingredient, a flavoring agent or a pigment.

14. The composition of claim 12, wherein said medicinal ingredient is a tooth caries preventative, an antibiotic, a vitamin, an enzyme or an anti-inflammatory agent.

15. The composition of claim 12, wherein said coating comprises agar as the main component.

16. The composition of claim 12, wherein said capsules have an average particle size of 0.5 to 3 mm.

17. The composition of claim 12, wherein said agar comprises 1 to 30% by weight of said capsule.

18. The composition of claim 12, wherein said coating further comprises a hydrophilic or lipophilic polymer.

19. The composition of claim 18, wherein said hydrophilic or lipophilic polymer is selected from the group consisting of gelatin, sodium alginate, carrageenan, carboxymethyl cellulose, methyl cellulose, hydroxyethyl cellulose, hydroxypropyl cellulose, hydroxypropylmethyl cellulose, gum arabic, gum guar, gum xanthane, casein, pectin, albumin, polyvinyl alcohols, polyethylenes, polypropylenes, polystyrenes, polyvinyl chlorides, polyacrylic acids, polymethacrylic acids, cetyl alcohol, stearyl alcohol, ethylene glycol distearate, sorbitan tristearate, ceresin, paraffin waxes, polyolefin waxes, beeswaxes and carnauba wax.

20. The composition of claim 18, wherein said coating comprises 100 parts by weight of said agar and 1 to 20 parts of said hydrophilic or lipophilic polymer.

21. The composition of claim 12, wherein said surfactant is selected from the group consisting of polyoxyethylene-polyoxypropylene block copolymers, sucrose fatty acid esters, alkylglycosides, polyoxyethylene sucrose fatty acid esters and polyoxyethylene hydrogenated castor oils.

22. The composition of claim 12, wherein said abrasives comprise granules having a particle size of 50 to 500 μm.

23. The composition of claim 12, having a degree of transparency of not less than 3 mm.

* * * * *